United States Patent
Johnson et al.

(10) Patent No.: US 10,618,805 B2
(45) Date of Patent: Apr. 14, 2020

(54) METHOD TO REDUCE PORE DIAMETER USING ATOMIC LAYER DEPOSITION AND ETCHING

(71) Applicant: Applied Materials, Inc., Santa Clara, CA (US)

(72) Inventors: Joseph R. Johnson, Redwood City, CA (US); Kenichi Ohno, Sunnyvale, CA (US)

(73) Assignee: APPLIED MATERIALS, INC., Santa Clara, CA (US)

(*) Notice: Subject to any disclaimer, the term of this patent is extended or adjusted under 35 U.S.C. 154(b) by 0 days.

(21) Appl. No.: 16/122,183

(22) Filed: Sep. 5, 2018

(65) Prior Publication Data

US 2019/0092633 A1    Mar. 28, 2019

Related U.S. Application Data

(60) Provisional application No. 62/561,944, filed on Sep. 22, 2017.

(51) Int. Cl.
| | |
|---|---|
| *B82B 3/00* | (2006.01) |
| *G01N 33/487* | (2006.01) |
| *B82B 1/00* | (2006.01) |
| *B81C 1/00* | (2006.01) |

(52) U.S. Cl.
CPC ........ *B82B 3/0019* (2013.01); *B81C 1/00087* (2013.01); *B82B 1/001* (2013.01); *G01N 33/48721* (2013.01); *B81B 2203/0127* (2013.01)

(58) Field of Classification Search
CPC ... B81C 1/00087; B82B 1/001; B82B 3/0019; B81B 2203/0127
See application file for complete search history.

(56) References Cited

U.S. PATENT DOCUMENTS

| | | |
|---|---|---|
| 2009/0233395 A1 | 9/2009 | Pyo et al. |
| 2012/0108068 A1 | 5/2012 | Lytle |

(Continued)

FOREIGN PATENT DOCUMENTS

| | | |
|---|---|---|
| JP | 2009094279 A | 4/2009 |
| KR | 19990039740 A | 6/1999 |
| KR | 20070063148 A | 6/2007 |

OTHER PUBLICATIONS

International Seach Report and Written Opinion dated Jan. 2, 2019 for Application No. PCT/US2018/050405.

(Continued)

*Primary Examiner* — Hsien Ming Lee
(74) *Attorney, Agent, or Firm* — Patterson & Sheridan, LLP

(57) ABSTRACT

Methods are provided for manufacturing well-controlled, solid-state nanopores and arrays of well-controlled, solid-state nanopores by a cyclic process including atomic layer deposition (ALD), or chemical vapor deposition (CVD), and etching. One or more features are formed in a thin film deposited on a topside of a substrate. A dielectric material is deposited over the substrate having the one or more features in the thin film. An etching process is then used to etch a portion of the dielectric material deposited over the substrate having the one or more features in the thin film. The dielectric material deposition and etching processes are optionally repeated to reduce the size of the features until a well-controlled nanopore is formed through the thin film on the substrate.

11 Claims, 4 Drawing Sheets

(56) References Cited

U.S. PATENT DOCUMENTS

| | | | |
|---|---|---|---|
| 2013/0344699 A1* | 12/2013 | Chiba | H01L 21/02118 438/700 |
| 2014/0262820 A1 | 9/2014 | Kuan et al. | |
| 2015/0108008 A1 | 4/2015 | Kwok et al. | |

OTHER PUBLICATIONS

Liu, Zewen, et al., "Solid-State Nanopore-Based DNA Sequencing Technology", Journal of Nanomaterials, May 2016, pp. 1-13.

Yanagi, Itaru, et al.,"Fabrication of 3-nm-thick Si3N4 membranes for solid-state nanopores using the poly-Si sacrificial layer process", Scientific Reports, Oct. 2015, pp. 1-13.

Archer, Marie J., et al., "Fabrication and Characterization of Silicon Micro-Funnels and Tapered Micro-Channels for Stochastic Sensing Applications", Sensors, Jun. 2008, pp. 3848-3872.

Gadgil, V. J., et al., "Fabrication of nano structures in thin membranes with focused ion beam technology", Surface & Coatings Technology, Mar. 2009, pp. 2436-2441.

Kwok, Harold, et al., "Nanopore Fabrication by Controlled Dielectric Breakdown", Plos One, Mar. 2014, pp. 1-6.

Venkatesan, Bala Murali, et al., "Highly Sensitive, Mechanically Stable Nanopore Sensors for DNA Analysis", Advanced Materials, Jul. 2009, pp. 2771-2776.

Schneider, Gregory F., et al., "DNA translocation through Graphene Nanopore", Kavli Institute of Nanoscience, 2010, pp. 3163-3167.

Goto, Yusuke, et al., "Integrated solid-state nanopore platform for nanopore fabrication via dielectric breakdown, DNA-speed deceleration and noise reduction", Scientific Reports, Aug. 2016, pp. 1-8.

Dela Torre, Ruby, et al., "Fabrication and characterization of solid-state nanopore arrays for high-throughput DNA sequencing", Nanotechnology, Sep. 2012, pp. 1-6.

Zeng, Shuangshuang et al., "Rectification of protein translocation in truncated pyramidal nanopores", Nature Nanotechnology, Oct. 2019, pp. 1056-1062.

\* cited by examiner

METHOD TO REDUCE PORE DIAMETER USING ATOMIC LAYER DEPOSITION AND ETCHING

CROSS-REFERENCE TO RELATED APPLICATIONS

This application claims benefit of U.S. Provisional Patent Application Ser. No. 62/561,944, filed on Sep. 22, 2017, which is herein incorporated by reference in its entirety.

BACKGROUND

Field

Aspects disclosed herein relate to methods of manufacturing well-controlled, solid-state nanopores and arrays of well-controlled, solid-state nanopores by cyclic atomic layer deposition (ALD), or chemical vapor deposition (CVD), and etching.

Description of the Related Art

Nanopores are widely used for applications such as deoxyribonucleic acid (DNA) and ribonucleic acid (RNA) sequencing. In one example, nanopore sequencing is performed using an electrical detection method, which generally includes transporting an unknown sample through the nanopore, which is immersed in a conducting fluid, and applying electric potential across the nanopore. Electric current resulting from the conduction of ions through the nanopore is measured. The magnitude of the electric current density across a nanopore surface depends on the nanopore dimensions and the composition of the sample, such as DNA or RNA, which is occupying the nanopore at the time. Different nucleotides cause characteristic changes in electric current density across nanopore surfaces. These electric current changes are measured and used to sequence the DNA or RNA sample.

Various methods have been used for biological sequencing. Sequencing by synthesis, or second generation sequencing, is used to identify which bases have attached to a single strand of DNA. Third generation sequencing, which generally includes threading an entire DNA strand through a single pore, is used to directly read the DNA. Some sequencing methods require the DNA or RNA sample to be cut up and then reassembled. Additionally, some sequencing methods use biological membranes and biological pores, which have shelf lives and must be kept cold prior to use.

Solid-state nanopores, which are nanometer-sized pores formed on a free-standing membrane such as silicon nitride or silicon oxide, have recently been used for sequencing. Current solid-state nanopore fabrication methods, such as using a tunneling electron microscope, focused ion beam, or electron beam, however, cannot easily and cheaply achieve the size and position control requirements necessary for manufacturing arrays of nanopores. Additionally, current nanopore fabrication methods are time consuming.

Therefore, there is a need in the art for improved methods of manufacturing a well-controlled, solid-state nanopore and arrays of well-controlled, solid-state nanopores.

SUMMARY

Methods are provided for manufacturing well-controlled, solid-state nanopores and arrays of well-controlled, solid-state nanopores by a cyclic process including atomic layer deposition (ALD), or chemical vapor deposition (CVD), and etching. One or more features are formed in a thin film deposited on a topside of a substrate. A dielectric material is deposited over the substrate having the one or more features in the thin film. An etching process is then used to etch a portion of the dielectric material deposited over the substrate having the one or more features in the thin film. The dielectric material deposition and etching processes are optionally repeated to reduce the size of the features until a well-controlled nanopore is formed through the thin film on the substrate.

In one aspect, a method for forming a nanopore is provided. The method includes providing a substrate having at least one feature formed in a thin film deposited on a topside thereof, the feature having one or more sidewalls and a bottom, depositing a first amount of dielectric material over the substrate having the at least one feature and etching a first portion of the first amount of dielectric material on the bottom of the at least one feature.

In another aspect, a method for forming a nanopore is provided. The method includes providing a substrate having at least one feature formed in a thin film deposited on a topside thereof, the feature having one or more sidewalls and a bottom, depositing a first amount of dielectric material over the substrate having the at least one feature, etching a first portion of the first amount of dielectric material on the bottom of the at least one feature, depositing a second amount of dielectric material over the substrate having the at least one feature, and etching a second portion of the second amount of dielectric material on the bottom of the at least one feature to form at least one nanopore.

In yet another aspect, a substrate is provided. The substrate includes a first silicon layer and a second silicon layer, an dielectric layer disposed between the first silicon layer and the second silicon layer; and a thin film disposed over the second silicon layer. The thin film includes at least one first feature formed therethrough, the at least one first feature having one or more sidewalls and a bottom, a plurality of second features formed therethrough, each of the plurality of second features having one or more sidewalls and a bottom, and a dielectric material disposed on the sidewalls of the at least one first feature and the sidewalls of the plurality of second features such that the at least one first feature has a first diameter and the plurality of second features have a second diameter, the first diameter being less than the second diameter, the first diameter corresponding to a nanopore formed in the thin film.

BRIEF DESCRIPTION OF THE DRAWINGS

So that the manner in which the above recited features of the present disclosure can be understood in detail, a more particular description of the disclosure, briefly summarized above, may be had by reference to aspects, some of which are illustrated in the appended drawings. It is to be noted, however, that the appended drawings illustrate only exemplary aspects and are therefore not to be considered limiting of its scope, and may admit to other equally effective aspects.

To facilitate understanding, identical reference numerals have been used, where possible, to designate identical elements that are common to the figures. It is contemplated that elements and features of one aspect may be beneficially incorporated in other aspects without further recitation.

DETAILED DESCRIPTION

Methods are provided for manufacturing well-controlled, solid-state nanopores and arrays of well-controlled, solid-state nanopores by a process including atomic layer deposition (ALD) and etching. One or more features are formed in a thin film deposited on a topside of a substrate. A dielectric material is deposited over the substrate having the one or more features in the thin film using ALD. An etching process is then used to etch a portion of the dielectric material deposited over the substrate having the one or more features in the thin film. The dielectric material ALD and etching processes are repeated to reduce the size of the features until a well-controlled nanopore is formed through the thin film on the substrate.

Methods described herein refer to formation of nanopores on a semiconductor substrate as an example. It is also contemplated that the described methods are useful to form other pore-like structures on various materials, including solid-state and biological materials. Methods described herein refer to formation of one or more trenches or tubes as examples; however, other etched features and any combinations thereof are also contemplated. For illustrative purposes a silicon on insulator (SOI) substrate with a silicon oxide layer is described; however, any suitable substrate materials and dielectric materials are also contemplated. Additionally, methods described herein refer to a topside and a backside of the substrate. The topside and backside generally refer to opposite sides of the substrate and do not necessarily refer to an upward or downward orientation.

Figure 1:
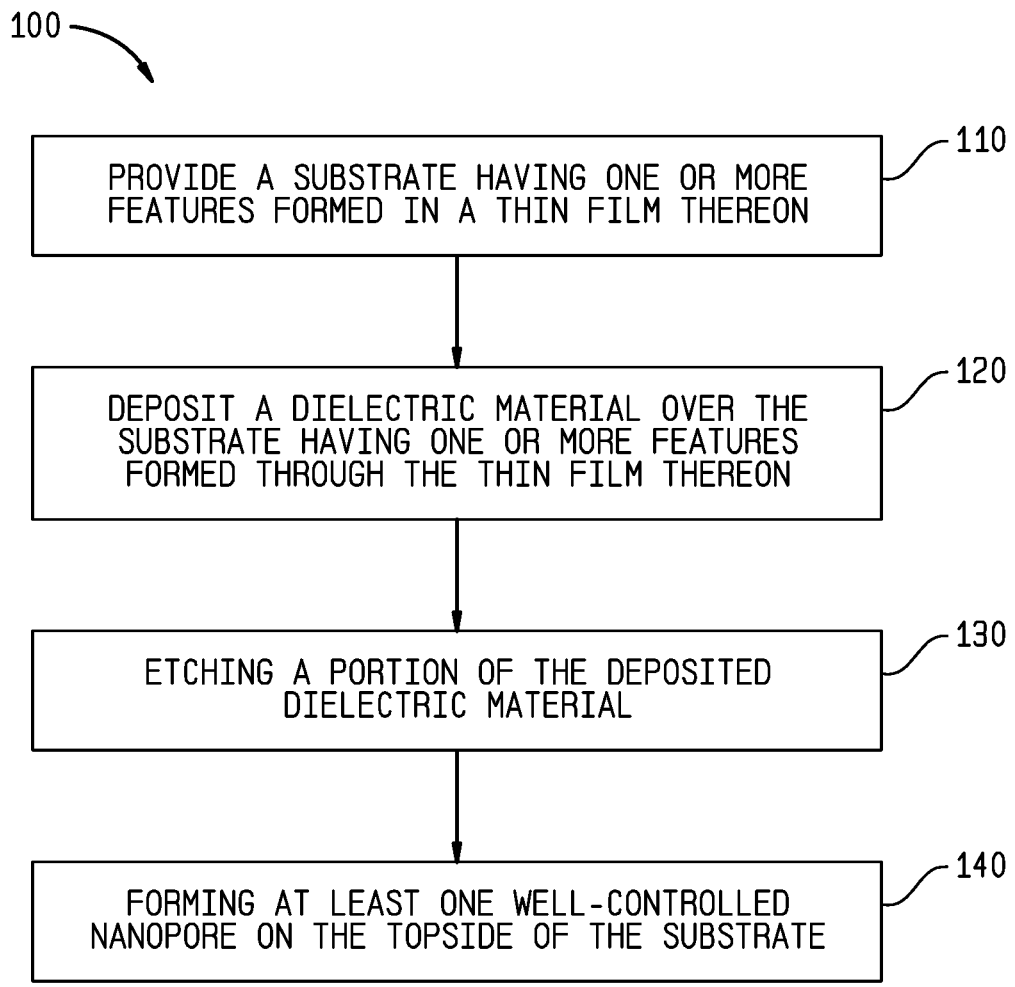
FIG. 1 is a process flow of a method for forming one or more nanopores according to the present disclosure.

FIG. 1 is a process flow of a method 100 for forming one or more nanopores according to the present disclosure. Prior to method 100, a substrate is processed. A thin film is deposited over a topside of the substrate and one or more features are patterned in the thin film over the topside of the substrate. At operation 110, the substrate having one or more features patterned in the thin film over the topside of the substrate is provided. At operation 120, a first amount of dielectric material is deposited over the substrate having one or more features in the thin film on the topside thereof. At operation 130, a portion of the deposited dielectric material is etched, such as the portion of deposited dielectric material at the bottom of the one or more features. A portion of the deposited dielectric material, such as the portion of deposited dielectric material on the one or more sidewalls of the one or more features, remains on the substrate. Operation 120 and operation 130 are optionally cyclically repeated until a well-controlled nanopore is formed on the topside of the substrate at operation 140. For example, in one aspect, a second amount of dielectric material is deposited over the substrate having the one or more features patterned in the thin film thereof and then a portion of the second amount of dielectric material is etched from the substrate. In one example, the dielectric material deposition and etching processes are repeated any suitable number of times to form a well-controlled nanopore. In further examples, one full cycle of deposition and etching will be suitable to form a well-controlled nanopore at or near the center of the one or more features The substrate is generally any suitable substrate, such as a doped or undoped silicon (Si) substrate. The thin film deposited over the topside of the substrate is generally any suitable thin film. The thin film is generally deposited by any suitable deposition process, including but not limited to, atomic layer deposition or chemical vapor deposition and is of any suitable thickness. Patterning the one or more features in the deposited dielectric thin film is accomplished by any suitable patterning process, including but not limited to, standard photolithography. The one or more features that are patterned are generally any suitable size and shape, such as trenches or tubes. In one aspect, the one or more features are of various width, such as a first width and a second width, or of various diameters, such as a first diameter and a second diameter. Any suitable etching process is generally used to etch the portion of the dielectric materials. Suitable etching processes include, but are not limited to, dry etching processes, for example reactive ion etching (RIE). Operation 120 and operation 130 are optionally repeated any suitable number of times to form a well-controlled nanopore at or near a center of the one or more features. In some aspects, one full cycle of deposition and etching will be suitable to form a nanopore at or near the center of the one or more features; however, in other aspects, multiple repetitions of the cycles will be suitable to form a nanopore at the center of the one or more features, depending on the size of the nanopore to be formed. Further substrate processing may be performed at the conclusion of method 100. For example, a selective etch process may be used to remove a portion of the substrate.

FIGS. 2A-2K depict cross-sectional views of a substrate 200 on which one or more nanopores are formed according to a process flow disclosed herein, such as at various stages of the process flow 100.

Figure 2A:
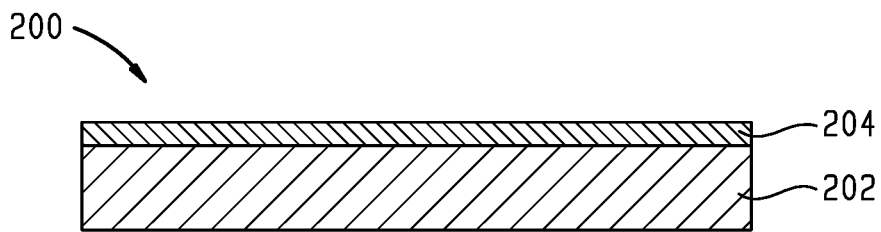
FIGS. 2A-2K depict cross-sectional views of a substrate on which one or more nanopores are formed at various stages of a process flow disclosed herein.
Figure 2B:
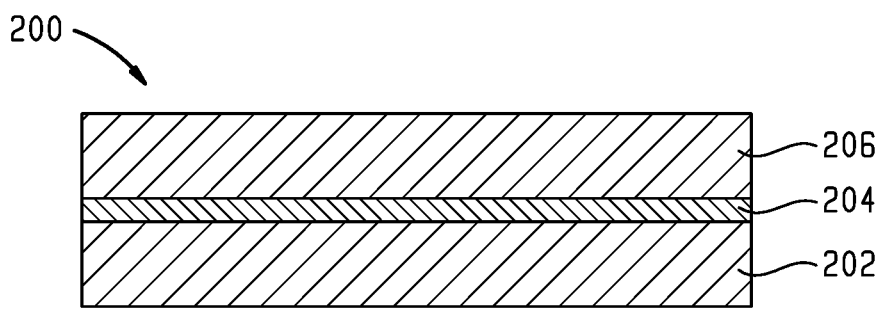

As shown in FIG. 2A, a dielectric layer 204 is deposited over a first Si layer 202. As shown in FIG. 2B, a second Si layer 206 is deposited over the dielectric layer 204 to provide a silicon on insulator (SOI) substrate.

Figure 2C:
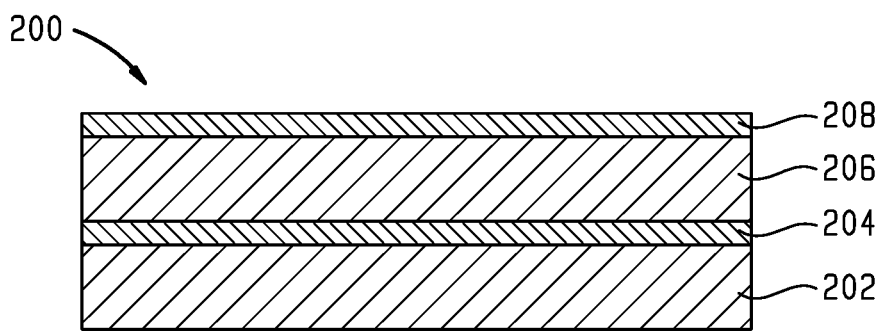

A thin film 208 is then deposited over the second Si layer 206, as shown in FIG. 2C. The thin film 208 is generally deposited by any suitable deposition process, including but not limited to ALD, and generally has a thickness between about 1 nanometer (nm) and about 10 nm, for example between about 2 nm about 6 nm, such as about 5 nm. In the example of FIG. 2C, the thin film 208 is a silicon-containing film.

Figure 2D:
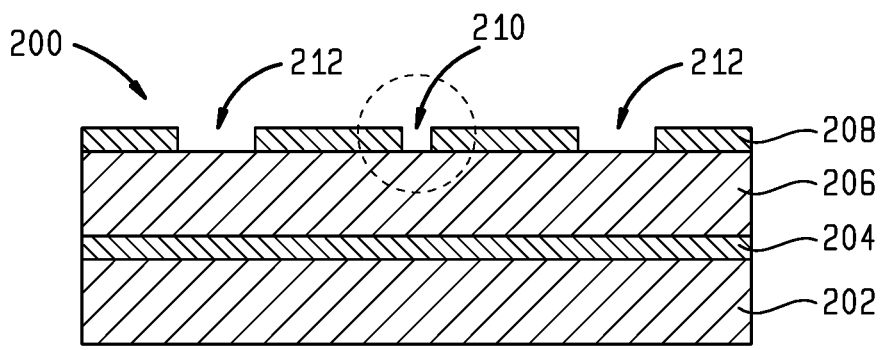
Figure 2E:
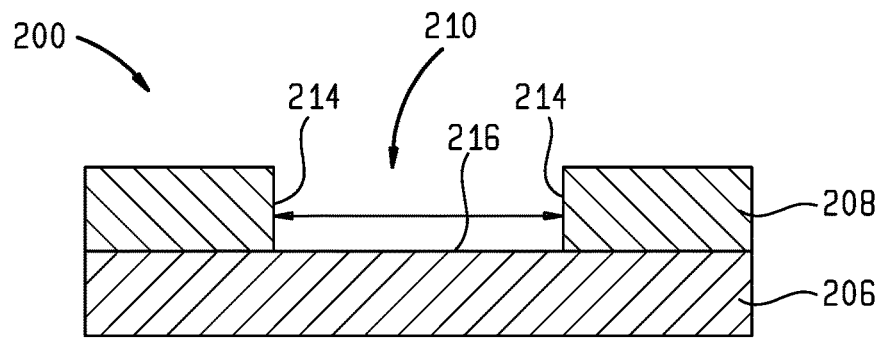

As shown in FIG. 2D, the thin film 208 is patterned with at least one first feature 210 (one is shown) and one or more second features 212 (two are shown). In the example of FIG. 2D, the first feature 210 has a first width or diameter and the second features 212 have a second width or diameter. The first feature 210 includes one or more sidewalls 214 and a bottom 216, which corresponds to a first surface of the second Si layer 206, as shown in FIG. 2E, which is an enlarged portion of FIG. 2D. The first width or diameter is generally between about 10 nanometers (nm) and about 100 nm, for example, between about 20 nm and about 60 nm, such as about 50 nm. The second width or diameter is generally between about 0.5 microns (μm) and about 100 μm, such as about 1 μm.

Figure 2F:
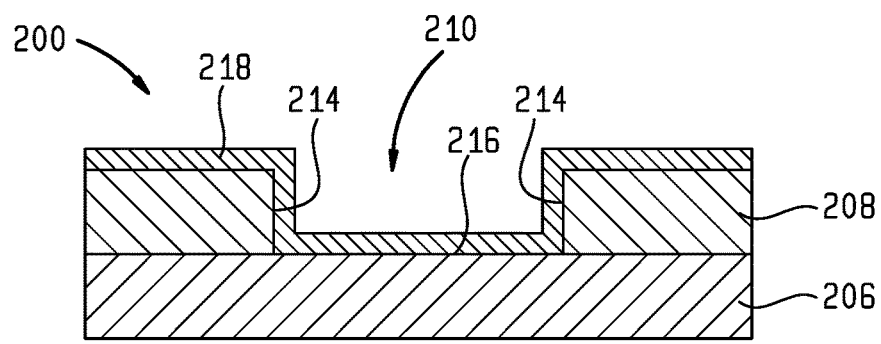

A dielectric material 218 is deposited over the substrate 200, as shown in FIG. 2F. The dielectric material 218 is generally conformally deposited by ALD or CVD and covers the thin film 208 as well as the exposed portion of the second Si layer 206, or bottom 216 of the one or more first features 210.

Figure 2G:
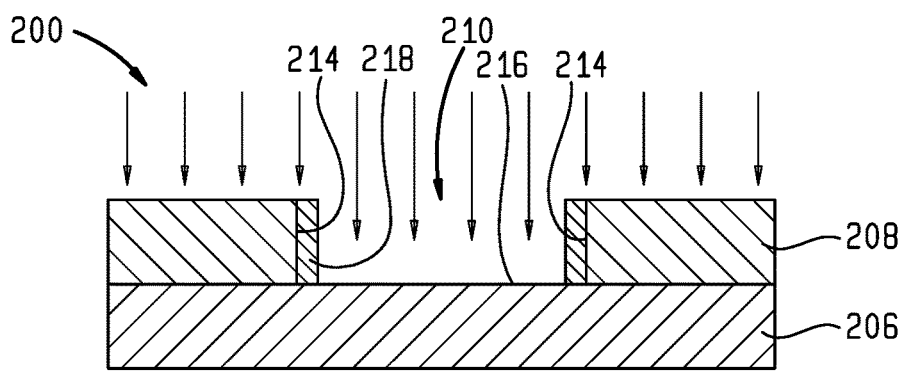

An RIE etching process is then performed to remove a portion of the dielectric material 218, as shown in FIG. 2G. The RIE generally removes a portion of the dielectric material 218 on the bottom 216 of the first feature 210, or the first surface of the second Si layer 206 and does not etch the dielectric material 218 deposited on the sidewalls 214.

Figure 2H:
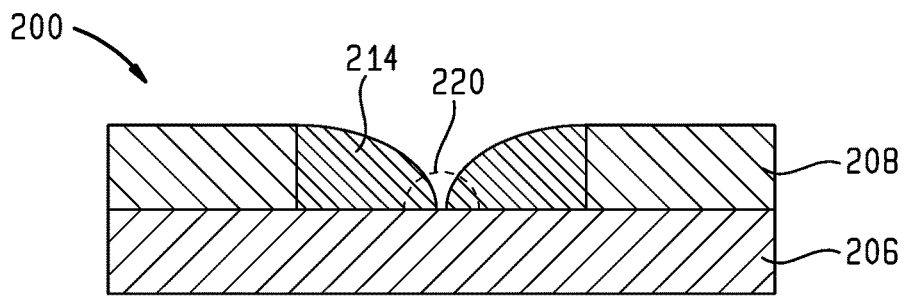
Figure 2I:
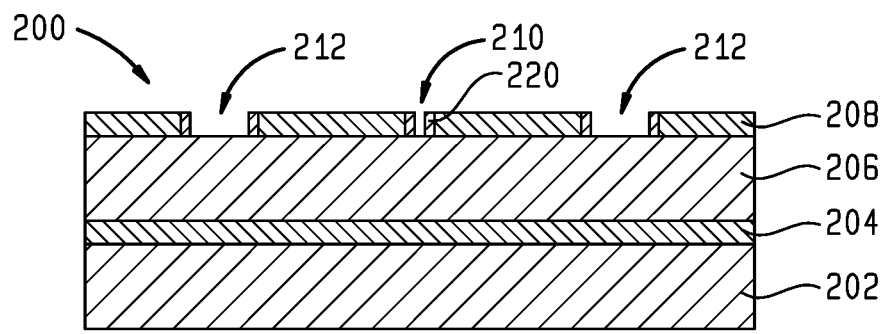

The ALD or CVD of dielectric material and subsequent RIE etch are optionally cyclically repeated until a nanopore 220 is formed at or near the center of each of the one or more first features 210, as shown in FIG. 2G and FIG. 2H. As shown in the example of FIG. 2H, the cyclic processes generally form a funnel-shaped gap between the dielectric material 218 deposited on the sidewalls 214. The nanopore 220 is generally formed at the bottom of the funnel-shaped gap at or near the center of the first feature 210.

By using cyclic ALD and etch processes, the dielectric material 218 is selectively deposited on the sidewalls 214 of the first features 210 formed on the substrate 200. Being able to selectively deposit the dielectric material 218 on the sidewalls 214 provides the ability to shrink the size of the nanopore 220 very controllably. A well-controlled size of the nanopore 220 is generally a diameter or width suitable for sequencing a sample of a certain size. In one aspect, the size of the nanopore 220 is about 100 nm or less, such as 50 nm or less. In one aspect, the size of the nanopore 220 is between about 0.5 nm and about 5 nm, for example between about 1 nm and about 3 nm, such as 2 nm. In another aspect, the size of the nanopore 220 is between about 1.5 nm and about 1.8 nm, such as about 1.6 nm, which is roughly the size of a single strand of DNA. In another aspect, the size of the nanopore 220 is between about 2 nm and about 3 nm, such as about 2.8 nm, which is roughly the size of double-stranded DNA. A well-controlled position of the nanopore 220 is generally any position on the substrate which is suitable for configuration of one or more nanopores. The disclosed deposition and etch processes also allow the length of the nanopore to remain constant, which provides for improved signal-to-noise ratio during processes, such as DNA sequencing. Additionally, methods disclosed herein are generally used to control the position of each of the one or more nanopores 220 such that a nanopore array of desired configuration for sequencing or other processes is formed.

Figure 2J:
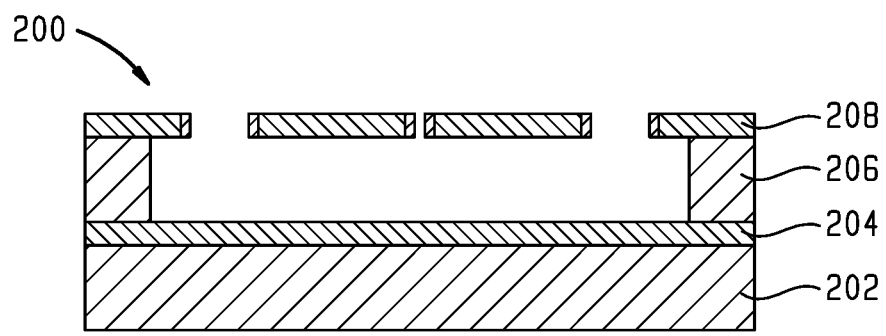
Figure 2K:
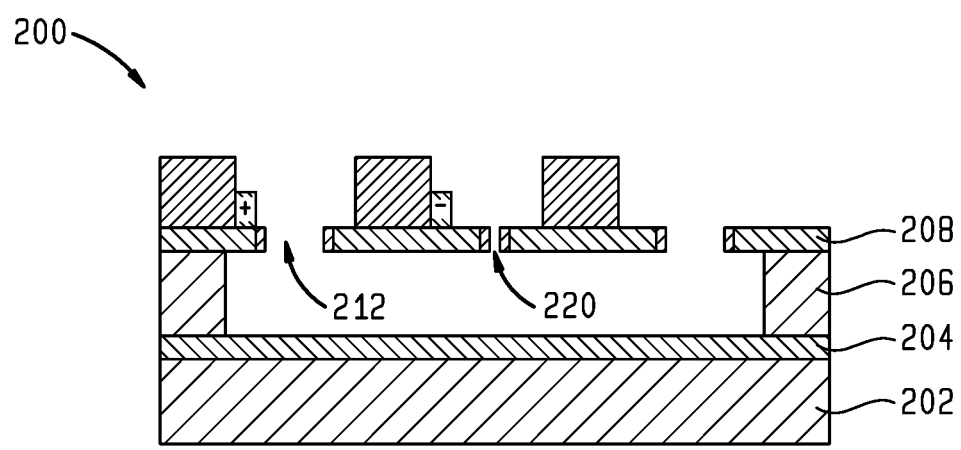

The substrate 200 may be further processed after the one or more nanopores 220 are formed. For example, a portion of the second Si layer 206 may be selectively etched such that a thin film membrane of thin film 208 have one or more nanopores 220 formed therein remains, as shown in FIG. 2J. One or more additional layers may be deposited over at least a portion of the thin film membrane, for example a silicon nitride (SiN) layer and positive and negative electrodes, for sequencing processes, as shown in FIG. 2K. The one or more additional layers may be deposited at any stage of the process flows disclosed herein.

Benefits of the present disclosure include the ability to quickly form well-controlled nanopores and nanopore arrays, which are generally individually addressable. Disclosed methods generally provide nanopores that are well-controlled in size and in position through a thin membrane. Methods of manufacturing nanopores of well-controlled size provide improved signal-to-noise ratios because the size of the nanopore is similar to the size of the sample, such as a single strand of DNA, being transmitted through the nanopore, which increases the change in electric current passing through the nanopore. Additionally, methods of manufacturing nanopores having well-controlled positions enables a sample, such as DNA, to freely pass through the nanopore. The thinness of the membrane, which is generally between about 1 nm and about 10 nm, for example between about 1 nm and about 5 nm, such as about 1 nm, provides for improved reading of the DNA sequence.

While the foregoing is directed to aspects of the present disclosure, other and further aspects of the disclosure may be devised without departing from the basic scope thereof, and the scope thereof is determined by the claims that follow.

What is claimed is:

1. A method for forming a nanopore, comprising:
   providing a substrate having at least one feature formed in a thin film deposited on a topside thereof, the at least one feature having one or more sidewalls and a bottom;
   depositing a first amount of dielectric material over the substrate having the at least one feature;
   etching a first portion of the first amount of dielectric material on the bottom of the at least one feature; and
   repeating the depositing of the first amount of dielectric material and the etching the first portion of the first amount of dielectric material on the bottom until at least one nanopore is formed between the first amount of dielectric material deposited on the one or more sidewalls at or near a center of at least one feature.

2. A method for forming a nanopore, comprising:
   providing a substrate having at least one feature formed in a thin film deposited on a topside thereof, the at least one feature having one or more sidewalls and a bottom;
   depositing a first amount of dielectric material over the substrate having the at least one feature; and
   etching a first portion of the first amount of dielectric material on the bottom of the at least one feature to form the nanopore on the topside of the substrate, wherein a size of the nanopore is less than about 100 nanometers.

3. The method of claim 2, wherein a size of the nanopore is less than about 50 nanometers.

4. A method for forming a nanopore, comprising:
   providing a substrate having at least one feature formed in a thin film deposited on a topside thereof, the at least one feature having one or more sidewalls and a bottom;
   depositing a first amount of dielectric material over the substrate having the at least one feature;
   etching a first portion of the first amount of dielectric material on the bottom of the at least one feature; and
   selectively removing a portion of the substrate underneath the at least one feature.

5. A method for forming a nanopore, comprising:
   providing a substrate having at least one feature formed in a thin film deposited on a topside thereof, the feature having one or more sidewalls and a bottom;
   depositing a first amount of dielectric material over the substrate having the at least one feature;
   etching a first portion of the first amount of dielectric material on the bottom of the at least one feature;
   depositing a second amount of dielectric material over the substrate having the at least one feature; and
   etching a second portion of the second amount of dielectric material on the bottom of the at least one feature to form at least one nanopore.

6. The method of claim 5, wherein depositing the first amount of dielectric material and depositing the second amount of dielectric material is accomplished by atomic layer deposition or chemical vapor deposition.

7. The method of claim 5, wherein etching the first portion of the first amount of dielectric material and etching the second portion of the second amount of dielectric material is accomplished by dry etching.

8. The method of claim 5, further comprising:
   depositing a third amount of dielectric material over the substrate having the at least one feature; and
   etching a third portion of the third amount of dielectric material on the bottom of the at least one feature to form at least one nanopore.

9. The method of claim 5, further comprising:
selectively removing a portion of the substrate underneath the at least one nanopore.

10. The method of claim 5, wherein a size of the nanopore is less than about 100 nanometers.

11. The method of claim 5, wherein a size of the nanopore is less than about 50 nanometers.

* * * * *